(12) United States Patent
Farnan

(10) Patent No.: US 12,097,334 B2
(45) Date of Patent: Sep. 24, 2024

(54) DILATION DELIVERY SYSTEM FOR A MEDICAL DEVICE

(71) Applicant: HeartWare, Inc., Miami Lakes, FL (US)

(72) Inventor: Robert C. Farnan, Fort Lauderdale, FL (US)

(73) Assignee: HeartWare, Inc., Miami Lakes, FL (US)

( * ) Notice: Subject to any disclaimer, the term of this patent is extended or adjusted under 35 U.S.C. 154(b) by 579 days.

(21) Appl. No.: 17/353,996

(22) Filed: Jun. 22, 2021

(65) Prior Publication Data

US 2021/0308420 A1    Oct. 7, 2021

Related U.S. Application Data

(63) Continuation of application No. 16/397,147, filed on Apr. 29, 2019, now Pat. No. 11,058,851, which is a
(Continued)

(51) Int. Cl.
*A61M 25/01* (2006.01)
*A61B 17/00* (2006.01)
(Continued)

(52) U.S. Cl.
CPC ......... *A61M 25/01* (2013.01); *A61B 17/3423* (2013.01); *A61B 17/3468* (2013.01);
(Continued)

(58) Field of Classification Search
CPC .............. A61M 25/0043; A61M 25/01; A61M 25/0169; A61M 25/0172; A61M 25/0194;
(Continued)

(56) References Cited

U.S. PATENT DOCUMENTS 5,114,407 A * 5/1992 Burbank ............ A61B 17/3496
604/164.12
5,263,937 A * 11/1993 Shipp ................. A61B 17/3417
606/167
(Continued)

FOREIGN PATENT DOCUMENTS

CN    203777464 U    8/2014
CN    204092788 U    1/2015
(Continued)

OTHER PUBLICATIONS

Prosecution History from U.S. Appl. No. 15/248,356 dated from Sep. 26, 2018 through Feb. 5, 2019, 32 pp.
(Continued)

*Primary Examiner* — Robert A Lynch
(74) *Attorney, Agent, or Firm* — Shumaker & Sieffert, P.A.

(57) ABSTRACT

A kit including a sheath having a tubular body with proximal and distal ends, an axis extending between the ends and a wall defining a bore extending along the axis to the distal end of the body. A delivery tube having proximal and distal ends and a lumen is adapted for disposition within the bore of the sheath in sealing engagement with the sheath, the delivery tube being slideable distally relative to the sheath. An elongated cannula having proximal and distal ends and a lumen is adapted for disposition inside the lumen of the delivery tube and an elongated dilator is adapted to fit within the lumen of the cannula with a proximal portion of the dilator extending proximally beyond the proximal ends of the cannula and delivery tube and in sealing engagement with the delivery tube proximal to the cannula.

19 Claims, 8 Drawing Sheets

Related U.S. Application Data continuation of application No. 15/248,356, filed on Aug. 26, 2016, now Pat. No. 10,315,006.

(60) Provisional application No. 62/211,127, filed on Aug. 28, 2015.

(51) Int. Cl.
*A61B 17/28* (2006.01)
*A61B 17/34* (2006.01)
*A61M 25/00* (2006.01)
*A61M 25/06* (2006.01)
*A61M 60/165* (2021.01)
*A61M 60/857* (2021.01)
*A61M 60/865* (2021.01)

(52) U.S. Cl.
CPC .... *A61M 25/0043* (2013.01); *A61M 25/0662* (2013.01); *A61M 60/165* (2021.01); *A61M 60/857* (2021.01); *A61M 60/865* (2021.01); *A61B 2017/00252* (2013.01); *A61B 17/28* (2013.01); *A61B 17/282* (2013.01); *A61B 2017/3425* (2013.01); *A61B 2017/347* (2013.01); *A61B 2017/3484* (2013.01); *A61M 2025/0681* (2013.01); *A61M 2025/0687* (2013.01); *A61M 2205/32* (2013.01)

(58) Field of Classification Search
CPC .......... A61M 25/0662; A61M 25/1006; A61M 2025/0681; A61M 2025/0687; A61M 2025/09008; A61M 60/165; A61M 60/857; A61M 60/865; A61M 2205/32; A61B 17/28; A61B 17/282; A61B 17/3421; A61B 17/3423; A61B 17/3462; A61B 17/3468; A61B 2017/00252; A61B 2017/3419; A61B 2017/3425; A61B 2017/345; A61B 2017/3464; A61B 2017/347; A61B 2017/348; A61B 2017/3482; A61B 2017/3484; A61B 2017/3488; A61B 2017/3492
See application file for complete search history.

(56) References Cited

U.S. PATENT DOCUMENTS

| | | | | |
|---|---|---|---|---|
| 5,350,393 A * | 9/1994 | Yoon | ................. | A61B 17/3496 604/164.12 |
| 5,354,302 A | 10/1994 | Ko | | |
| 5,676,670 A | 10/1997 | Kim | | |
| 5,797,888 A * | 8/1998 | Yoon | ................. | A61B 17/3421 604/249 |
| 5,824,002 A * | 10/1998 | Gentelia | ............ | A61B 17/3417 604/164.11 |
| 5,951,588 A | 9/1999 | Moenning | | |
| 6,428,550 B1 | 8/2002 | Vargas et al. | | |
| 6,436,119 B1 * | 8/2002 | Erb | .................... | A61B 17/3417 606/279 |
| 6,669,708 B1 | 12/2003 | Nissenbaum et al. | | |
| 6,843,795 B1 | 1/2005 | Houser et al. | | |
| 6,939,318 B2 * | 9/2005 | Stenzel | .............. | A61B 17/3468 604/60 |
| 7,357,807 B2 | 4/2008 | Donohoe et al. | | |
| 7,637,904 B2 * | 12/2009 | Wingler | ................. | A61B 17/43 604/533 |
| 7,713,193 B2 | 5/2010 | Nance et al. | | |
| 7,722,568 B2 | 5/2010 | Lenker et al. | | |
| 7,850,705 B2 | 12/2010 | Bachinski et al. | | |
| 8,337,394 B2 * | 12/2012 | Vakharia | ............ | A61B 1/00135 600/114 |
| 8,460,168 B2 | 6/2013 | Farnan | | |
| 8,905,961 B2 | 12/2014 | Braido et al. | | |
| 9,028,393 B2 | 5/2015 | Farnan | | |
| 10,315,006 B2 * | 6/2019 | Farnan | .............. | A61M 25/0662 |
| 11,058,851 B2 | 7/2021 | Farnan | | |
| 2002/0042622 A1 | 4/2002 | Vargas et al. | | |
| 2003/0130668 A1 | 7/2003 | Nieman et al. | | |
| 2004/0199177 A1 | 10/2004 | Kim | | |
| 2004/0236170 A1 | 11/2004 | Kim | | |
| 2007/0078504 A1 | 4/2007 | Mialhe | | |
| 2007/0244440 A1 * | 10/2007 | Pal | .................... | A61M 25/0074 604/164.13 |
| 2008/0027380 A1 | 1/2008 | Wholey et al. | | |
| 2009/0163872 A1 | 6/2009 | Tekulve | | |
| 2009/0254166 A1 | 10/2009 | Chou et al. | | |
| 2010/0160863 A1 | 6/2010 | Heuser | | |
| 2010/0249491 A1 | 9/2010 | Farnan et al. | | |
| 2013/0053941 A1 * | 2/2013 | Costello | .................. | A61F 2/966 623/1.11 |
| 2013/0066140 A1 | 3/2013 | McBride et al. | | |
| 2014/0277050 A1 * | 9/2014 | Andreas | ................ | A61F 11/202 606/185 |
| 2014/0371598 A1 | 12/2014 | Okubo et al. | | |

FOREIGN PATENT DOCUMENTS

| | | | |
|---|---|---|---|
| EP | 2233169 | A1 | 9/2010 |
| FR | 2853521 | A1 | 10/2004 |
| WO | 2007112033 | A2 | 10/2007 |

OTHER PUBLICATIONS

Prosecution History from U.S. Appl. No. 16/397,147, dated from Nov. 25, 2020 through Mar. 16, 2021, 44 pp.

China National Intellectual Property Administration, Dec. 31, 2019 Notice On The First Office Action for corresponding Chinese Application No. 201680049718.7, 16 pages.

International Search Report and Written Opinion dated Dec. 1, 2017, for corresponding International Application No. PCT/US2016/048939; International Filing Date: Aug. 26, 2016 consisting of 16—pages.

* cited by examiner

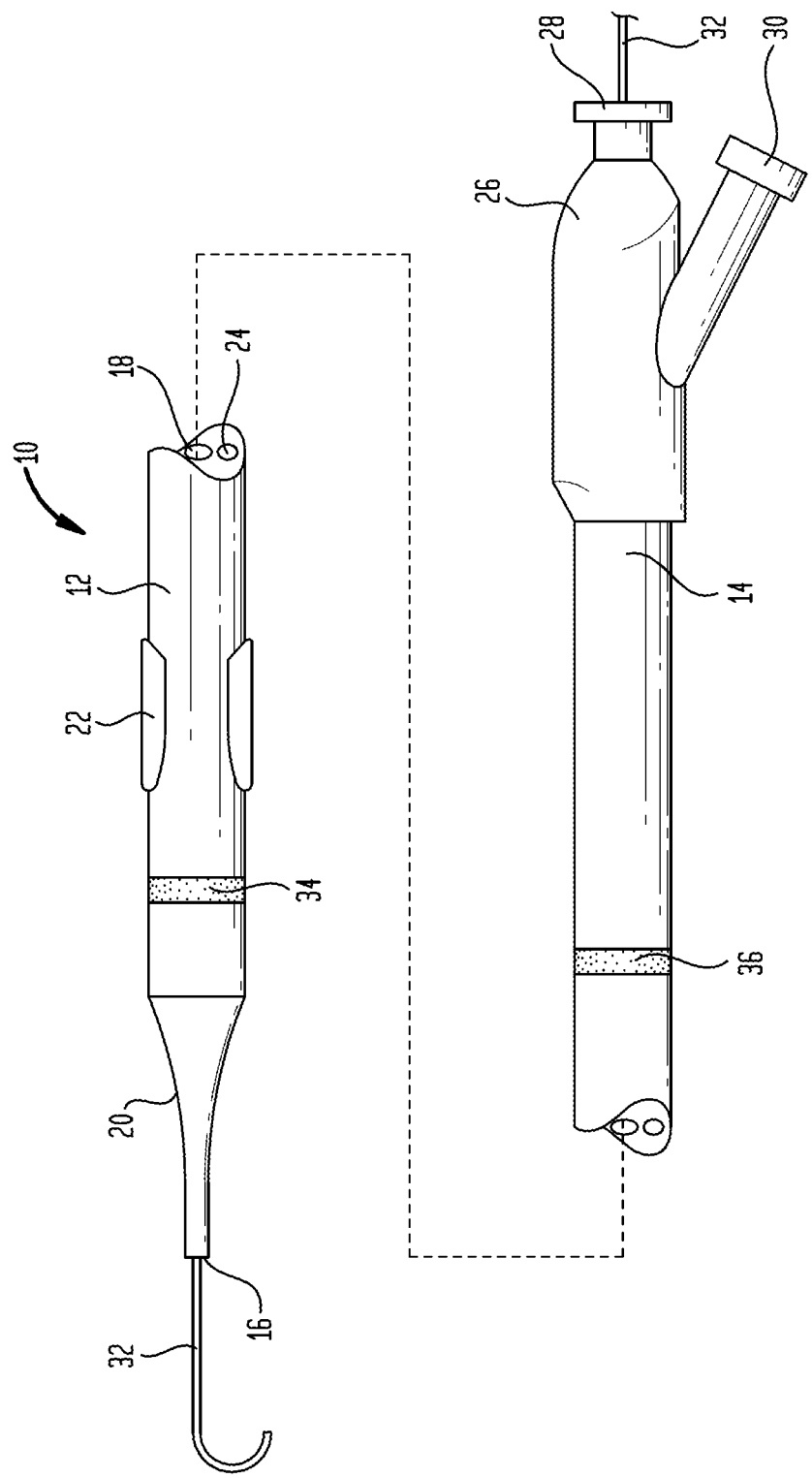

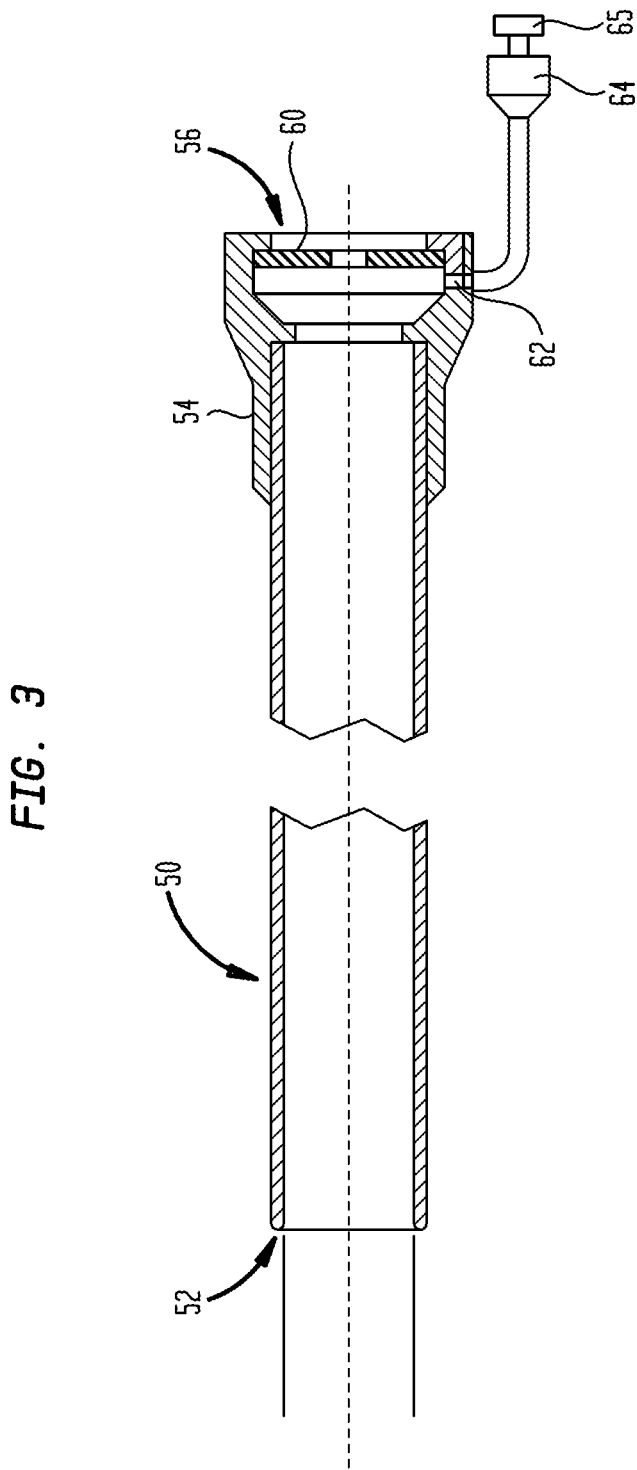

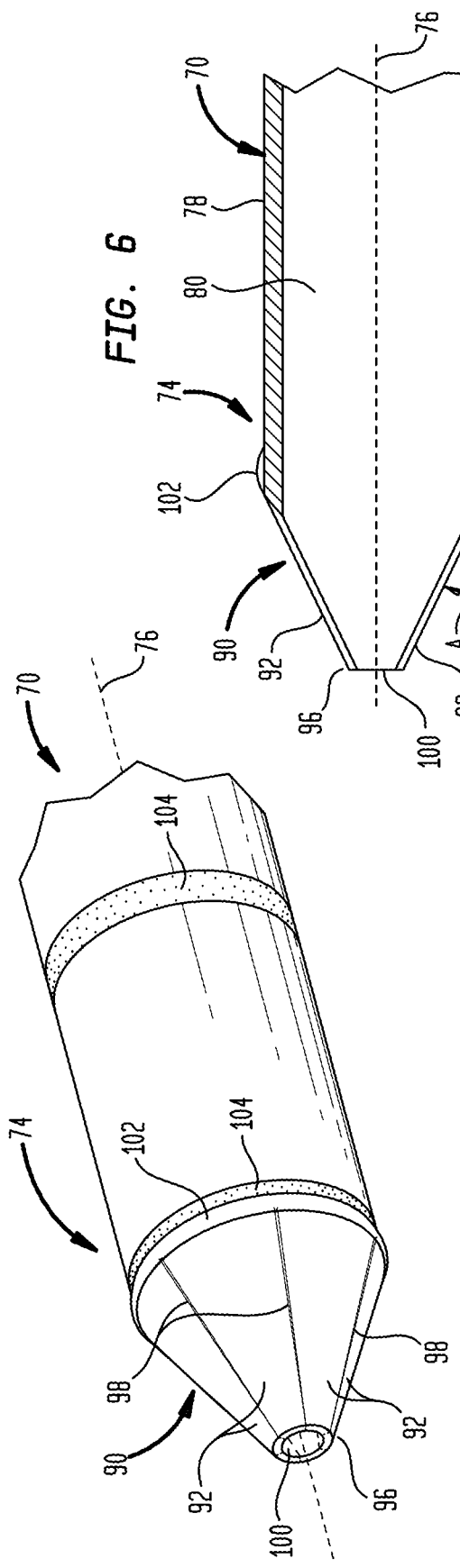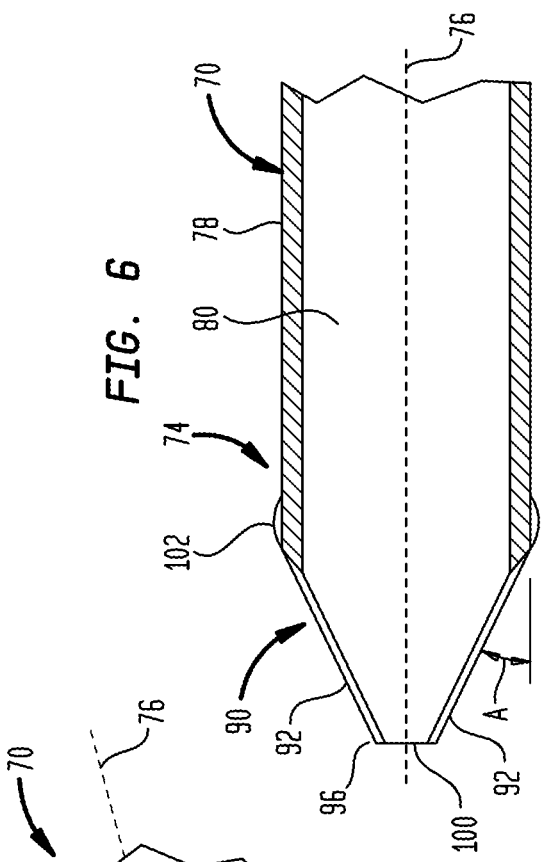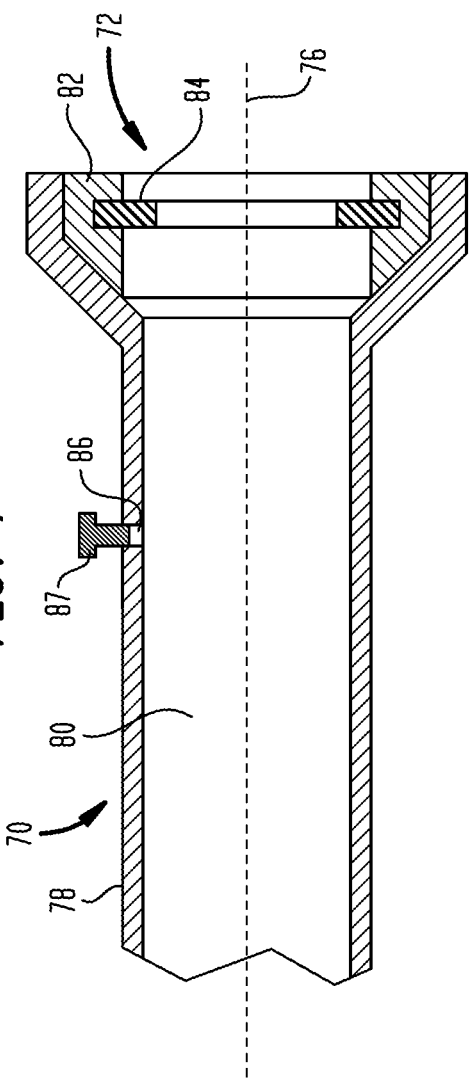

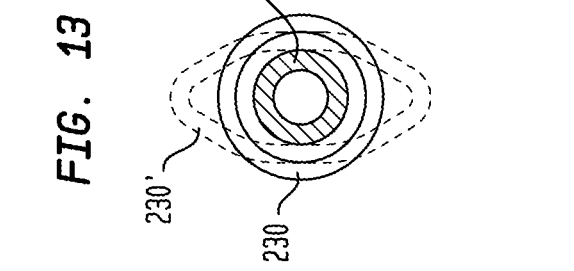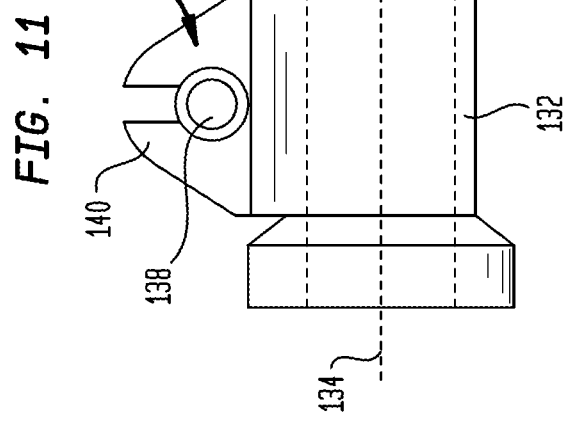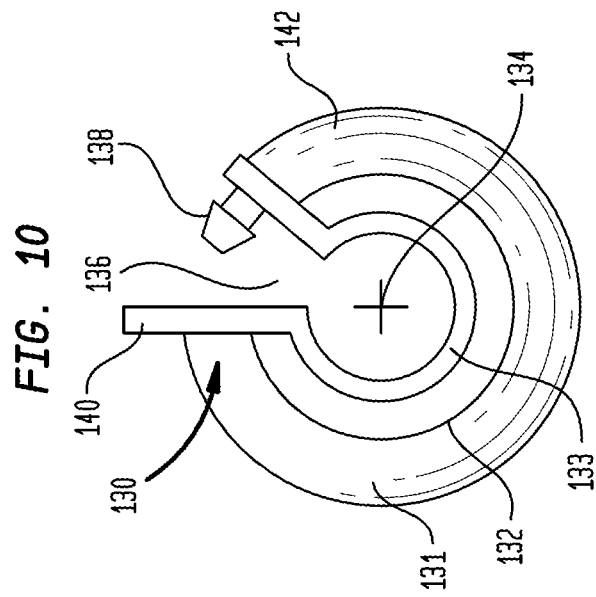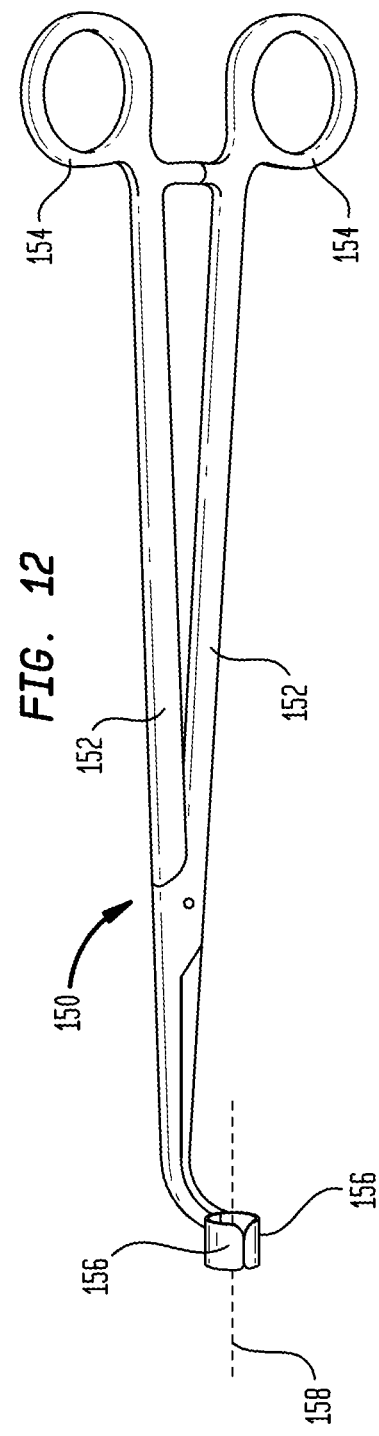

DILATION DELIVERY SYSTEM FOR A MEDICAL DEVICE

CROSS-REFERENCE TO RELATED APPLICATIONS

This application is a continuation of U.S. patent application Ser. No. 16/397,147, filed Apr. 29, 2019 and is a continuation of U.S. patent application Ser. No. 15/248,356, filed Aug. 26, 2016, now issued as U.S. Pat. No. 10,315,006, which application is related to and claims the benefit of the filing date of U.S. Provisional Patent Application No. 62/211,127 filed Aug. 28, 2015, the disclosure of which is hereby incorporated herein by reference.

BACKGROUND OF THE INVENTION

The present invention relates to delivery of medical devices to an operative site within the body and to systems and methods for the same.

It is often necessary to place medical devices within the body. For example, certain mechanical circulatory support devices ("MCSDs") use inlet cannulas to deliver blood from a chamber of the heart of a patient to a pump implanted within the body at a location remote from the heart. The pump pressurizes the blood and delivers it to an artery, thus assisting the pumping function of the heart. During installation of such an MCSD, the inlet cannula must be placed so that an end of the cannula projects through the wall of the appropriate heart chamber.

It is desirable to perform this procedure with only a minimum of surgical disruption to the patient's anatomy. For example, it would be desirable to install such a cannula through a limited thoracotomy. Although such a cannula can be installed by coring a hole in the wall of the heart chamber approximately the diameter of the cannula and then threading the cannula into the chamber through the cored hole, such a procedure requires measures to avoid life-threatening blood loss through the hole in the heart wall during installation. Thus, further improvement would be desirable.

SUMMARY OF THE INVENTION

One aspect of the invention provides a kit usable in implanting a cannula into a hollow organ. A kit according to this aspect of the invention desirably includes a sheath having a tubular body with proximal and distal ends and an axis extending between these ends. The sheath has a wall defining a bore extending along the axis to the distal end of the body and also has an end element disposed at the distal end of the bore. The end element desirably includes a plurality of flaps having proximal ends attached to the wall of the body at the distal end of the body and also having distal ends remote from the body. The flaps desirably have a closed position in which the flaps slope inwardly toward the axis from their proximal ends toward their distal ends, so that the flaps cooperatively define a surface tapering in the distal direction beyond the distal end of the body. For example, the flaps may define a conical surface. The flaps desirably are displaceable so as to move the distal ends of the flaps away from the axis and thus pivot the flaps to an open position. The kit according to this aspect of the invention desirably also includes a delivery tube. The delivery tube has proximal and distal ends and a lumen. The delivery tube desirably is adapted for disposition within the bore of the sheath, with the delivery tube in sealing engagement with the sheath and slideable relative to the sheath. Desirably, the delivery tube is slideable distally relative to the sheath from a disengaged position to an engaged position so as to force the flaps from the closed position to the open position as the delivery tube moves to the engaged position. The kit desirably also includes an elongated cannula adapted for disposition inside the lumen of the delivery tube and an elongated dilator adapted to fit within the lumen of the cannula. Desirably, the dilator is longer than the cannula, so that when the dilator is received in the cannula, a proximal portion of the dilator extends proximally beyond the proximal ends of the cannula and delivery tube, and this proximal portion desirably is in sealing engagement with the delivery tube at a point on the delivery tube proximal to the cannula. Desirably, the flaps of the sheath in the closed position define a hole at the distal end of the tapered surface, and the dilator has a distal end adapted to project distally beyond the distal end of the cannula and through the hole.

A further aspect of the invention provides an assembly. The assembly according to this aspect of the invention includes a fluid-tight enclosure defined at least in part by a sheath as discussed above and an elongated cannula contained entirely within the enclosure with the distal end of the cannula disposed adjacent the distal end of the sheath. An elongated shaft such as the shaft of a dilator as discussed above desirably is disposed within the lumen of the cannula with a proximal portion of the shaft extending proximally beyond the proximal end of the cannula, the shaft being sealingly engaged with the enclosure and slideable proximally and distally relative to the sheath. An assembly according to this aspect of the invention may include a delivery tube as discussed above, the proximal portion of the delivery tube in slideable sealing engagement with the sheath and the cannula being disposed within the delivery tube. In this embodiment, the delivery tube forms a portion of the enclosure. The enclosure may include one or more purge ports communicating with the interior of the enclosure and means for sealing the purge ports. As further discussed below, an assembly according to this aspect of the invention may be made using the elements of the kit discussed in connection with the foregoing aspect of the invention.

Yet another aspect of the invention provides a delivery sheath for a medical device. A delivery sheath according to this aspect of the invention includes a tubular body having proximal and distal ends, an axis extending between the ends, and a wall defining an exterior surface and a bore extending along the axis to the distal end of the body. Here again, an end element is disposed at the distal end of the bore and includes a plurality of flaps having proximal ends attached to the wall of the body at the distal end of the body and distal ends remote from the body, the flaps having a closed position in which the flaps slope inwardly toward the axis from their proximal ends towards their distal ends so that the flaps cooperatively define a surface tapering in the distal direction beyond the distal end of the body, the flaps being displaceable so as to move the distal ends of the flaps away from the axis and pivot the flaps to an open position. The sheath according to this aspect of the invention desirably includes a marker. The marker desirably includes at least one of the following: (1) a bump projecting outwardly from the exterior surface of the tubular body; and (2) a feature or features visualizable by fluoroscopic imaging, by ultrasonic imaging, or both, the marker being positioned at the distal end of the body. A sheath according to this aspect of the invention may be incorporated in the kits and assemblies as discussed above.

Yet another aspect of the present invention includes a kit comprising an elongated cannula having proximal and distal ends, a lumen, and an exterior surface and an expandable anchor mounted to the cannula at the distal end thereof. Desirably, the anchor is adapted for expansion within a hollow organ of a patient's body after insertion of the distal end of the cannula into the organ. The kit according to this aspect of the invention desirably includes an external securement device that is deformable from an open condition to a closed condition and is adapted to remain in the closed condition after deformation to the closed condition. The external securement device in the open condition desirably is adapted to at least partially surround the outside of the cannula and to slide freely along the cannula. The external securement device in the closed condition desirably is adapted to engage the outside of the cannula as, for example, to frictionally engage and grip the outside of the cannula. As further discussed below, the elements of the kit according to this aspect of the invention may be incorporated in a kit as discussed above or may be used separately.

Yet another aspect of the invention provides methods of connecting a cannula to a hollow organ of a patient's body. A method according to this aspect of the invention desirably includes the step of advancing a liquid-filled enclosure including a sheath having a tapered surface defined by a plurality of flaps at the distal end of the sheath, the enclosure entirely containing a hollow cannula having an expandable anchor at its distal end disposed adjacent the distal end of the sheath. The enclosure desirably is advanced in a distal direction toward the organ until the tapered surface of the sheath passes through the wall of the organ. The method desirably further includes the step of bringing the flaps of the sheath to an open position in which the flaps are separate from one another and the distal end of the sheath is in communication with the interior of the organ and advancing the cannula distally relative to the sheath, so that the anchor is positioned within the interior of the organ. The method desirably includes a subsequent step of expanding the anchor within the interior of the organ and withdrawing the enclosure proximally, away from the organ while leaving the cannula in place with the anchor inside the organ and a proximal portion of the cannula projecting from the organ. Desirably, the enclosure includes a delivery tube containing the cannula and the anchor, the delivery tube having an open distal end positioned adjacent the distal end of the sheath during the step of advancing the enclosure relative to the organ. The step of expanding the anchor within the interior of the organ may include advancing the cannula distally relative to the delivery tube so that the anchor passes out of the distal end of the delivery tube. Desirably, the distal end of the delivery tube is disposed immediately adjacent the flaps of the sheath during the initial step of advancing the enclosure relative to the organ so that upon completion of the initial advancement step, the distal end of the delivery tube is disposed within the interior of the organ. The step of bringing the flaps to the open position and advancing the cannula distally relative to the sheath can be performed by withdrawing the sheath proximally relative to the delivery tube while maintaining the distal end of the delivery tube in position within the interior of the organ.

As further discussed below, kits and methods according to the foregoing aspects of the invention provide simple methods of installing a cannula and anchoring the same in a hollow organ as, for example, in the atrium of the heart. These and other features and advantages of the present invention will be more readily apparent from the detailed description set forth below taken in conjunction with the accompanying drawings.

BRIEF DESCRIPTION OF THE DRAWINGS

FIG. 1 is a partially fragmentary elevational view of a dilator incorporated in a kit according to one embodiment of the invention.

FIG. 3 is a diagrammatic sectional view depicting a delivery tube used in the kit according to the embodiment of FIG. 1.

FIG. 5 is a fragmentary, diagrammatic perspective view of a sheath used in the kit according to the embodiment of FIG. 1.

FIGS. 6 and 7 are fragmentary, diagrammatic sectional view of the sheath shown in FIG. 5.

FIG. 10 is a diagrammatic end elevational view of a securement device usable in conjunction with the assembly of FIG. 8.

FIG. 11 is a diagrammatic side elevational view of the securement device shown in FIG. 10.

FIG. 12 is a plan view of a forceps usable with the components depicted in FIGS. 1-11.

FIG. 13 is a diagrammatic sectional view of a securement device and cannula according to a further embodiment of the invention.

DETAILED DESCRIPTION

Figure 2A:
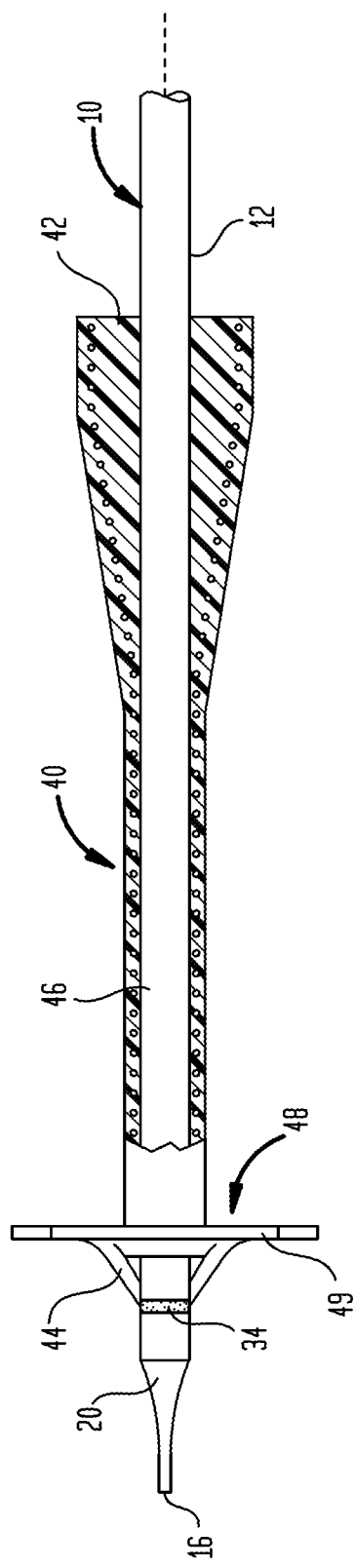
FIG. 2A is a diagrammatic elevational view of a cannula used in the kit according to the embodiment of FIG. 1.

FIG. 1 is a diagrammatic view of a dilator utilized in a kit according to one embodiment of the present invention. The dilator 10 includes an elongated shaft 12 having a proximal end 14 and a distal end 16. The dilator shaft 12 in this embodiment is of generally circular cross-section and may be, for example, about 5-6 mm in diameter. The dilator shaft has a guidewire lumen 18 extending from the proximal end 14 to the distal end 16. The exterior surface of the dilator shaft has a portion 10 tapering in the distal direction. That is, the cross-sectional dimensions of the shaft decrease in the distal direction, toward distal end 16, over the extent of tapering surface 20. A distal end marker 34, such as a stripe of contrasting color, desirably is provided adjacent the distal end of the dilator shaft between balloon 22 and tapering section 20. A proximal end marker 36 is provided adjacent the proximal end of the shaft. As discussed below, the markers are used to align the other elements of the system during assembly. Either or both of the markers optionally can be radiopaque for fluoroscopic visualization.

A balloon 22 is provided on the dilator shaft near the distal end, but proximal to the tapering surface 20. Balloon 22 may be provided as a unitary balloon completely surrounding the guidewire shaft or a one or more smaller balloons provided at one or more points around the circumference of the shaft.

Balloon 22 in the deflated condition depicted in FIG. 1 projects only slightly from the exterior surface of the dilator shaft. When inflated, balloon 22 projects further from the exterior surface of the shaft. An inflation lumen 24 extends from the proximal end 14 of the dilator shaft to balloon 22 and communicates with the balloon. A fitting 26 has a guidewire port 28 communicating with the guidewire lumen 18 and a separate port 30 communicating with inflation lumen 24, and thus with balloon 22.

During use, a guidewire 32 can be threaded through the guidewire port 28 and guidewire lumen 18, so that the guidewire extends entirely through the length of the dilator shaft. A syringe (not shown) or other source of fluid can be connected to inflation port 30 so that the syringe or other source can be used to selectively inflate and deflate balloon 22.

The dilator shaft desirably is formed from a polymeric material having some flexibility but also having substantial stiffness as, for example, a polymer having a hardness in the mid to upper part of the Shore D scale. The stiffness of the dilator shaft may vary along its length. For example, the proximal portion may be stiffer than the distal portion, so that during implantation the proximal portion will transmit distally-directed forces readily, and the distal portion will flex readily to follow a bend in a guidewire. Desirably, the dilator shaft has a hydrophilic surface with a low coefficient of friction. The balloon desirably has a high coefficient of friction. For example, if a low friction, hydrophilic coating is applied to the dilator shaft, the coating desirably is no applied to the balloon. Preferably, the dilator shaft is of constant diameter from its proximal end 14 to tapering section 20. The dilator shaft may have considerable length as, for example, twice the length of the cannula 40 discussed below or more; the dilator shaft is shown with portions removed in FIG. 1 for clarity of illustration.

The kit further includes an elongated cannula 40 (FIGS. 2A, 2B) having a proximal end 42, a distal end 44, and a lumen 46 extending between its proximal and distal ends. The lumen 46 typically is of constant diameter. The proximal end 42 of the cannula is of greater outside diameter than distal end 44. Desirably, the proximal portion of the cannula has progressively decreasing outside diameter in the distal direction, whereas the distal portion has a constant outside diameter. The distal portion is more flexible than the proximal portion. The cannula can be formed from a flexible material such as a soft polymer reinforced with a wire winding embedded in the wall of the cannula.

Figure 2B:
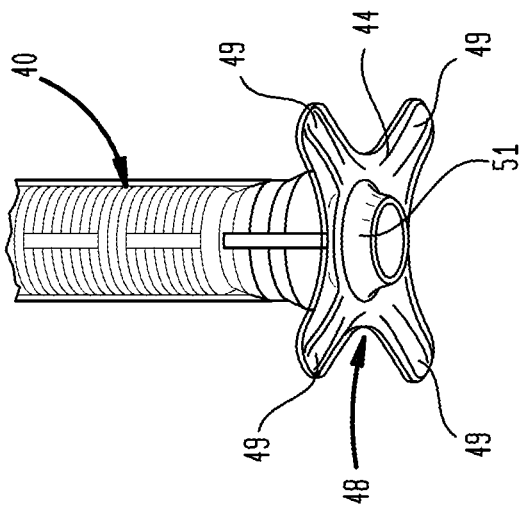
FIG. 2B is a diagrammatic perspective view depicting a portion of the cannula shown in FIG. 2A.

As best seen in FIG. 2B, the cannula further has an expandable anchor 48 adjacent its distal end. Anchor 48 desirably includes a central hub 51 formed from a rigid material plurality of resilient arms 49 attached to the hub. In the expanded condition of the anchor depicted in FIGS. 2A and 2B, the arms project from the cannula transverse to the axis of the cannula. In an assembled, ready-to-use condition of the kit, hereinafter referred to as the "operative" condition of the kit, the shaft 12 of dilator 10 is received within the lumen 46 of the cannula, with a proximal portion of the cannula shaft 12 projecting proximally beyond the proximal end 42 of the cannula and with the distal end 16 and with tapered section 20 projecting distally from the distal end 44 of the cannula. The dilator can be assembled in this position by aligning the distal end mark 34 on the dilator with the distal end 44 of the cannula.

In this condition, the balloon 22 (FIG. 1) on the dilator is disposed within lumen 46. Thus, by inflating the balloon, the balloon can be brought into forcible engagement with the wall of the cannula surrounding the lumen 46, so as to lock the cannula and dilator together. When the balloon is deflated, the cannula and dilator are slidable proximally and distally relative to one another.

The kit further includes an actuator in the form of a delivery tube 50 (FIG. 3). The delivery tube 50 desirably is a thin-walled tube formed from a relatively rigid material such as stainless steel. The tube has a rounded edge at its distal end 52 and has a fitting 54 at its proximal end 56. The length of delivery tube 50 is slightly greater than the length of the cannula; a portion of the delivery tube is removed in FIG. 3 for clarity of illustration. The delivery tube desirably has hydrophilic interior and exterior surfaces. For example, the tube can be covered with a coating of a hydrophilic material. Delivery tube 50 desirably has an interior diameter slightly larger than the maximum external diameter of the cannula 40 but smaller than the expanded diameter of anchor 48. (FIG. 2). For example, the interior diameter of the delivery tube may be on the order of 11-12 mm, whereas its wall thickness may be on the order of 0.2 mm, so that the delivery tube has an external diameter 0.4 mm larger than its internal diameter.

A flexible seal 60 is mounted to fitting 54. The seal may be an O-ring or a hemostatic valve. A purge port 62 extends through the wall of the fitting or through the wall of the delivery tube adjacent its proximal end. Purge port 62 is provided with a fitting 64 such as a Luer fitting for connection of a liquid source. A plug 65 is detachably mounted in fitting 64.

Figure 4A:
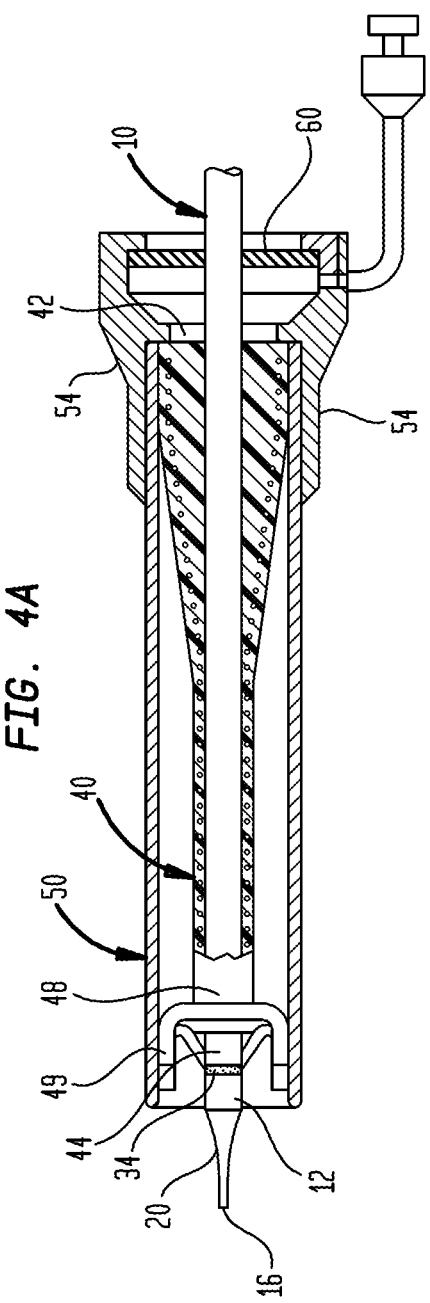
FIG. 4A is a diagrammatic sectional view depicting a subassembly including the components depicted in FIGS. 1-3.

In the assembled operative condition of the kit, the dilator 10, cannula 40, and delivery tube 50 form a subassembly depicted in FIG. 4A. In this condition, the cannula 40 is disposed entirely within the delivery tube. The distal end 44 of the cannula is disposed proximal to the distal end of the delivery tube. The expandable anchor 48 on the cannula is confined within the lumen of delivery tube 50. In this condition, the resilient arms constituting the anchor 48 are folded with their ends projecting distally as shown. Desirably, the ends of the anchor arms 48 are also disposed entirely within the interior of the delivery tube. The dilator 10 projects proximally through the seal 60 at the proximal end of the delivery tube and extends proximally from the delivery tube. Desirably, the shaft of the dilator is in slidable, sealing engagement with seal 60. The distal end 16 of the dilator projects distally beyond the distal end of the delivery tube. Most preferably, the tapered section 20 of the dilator, as well as a small portion of the constant diameter part of shaft 12, are disposed distal to the delivery tube.

Figure 4B:
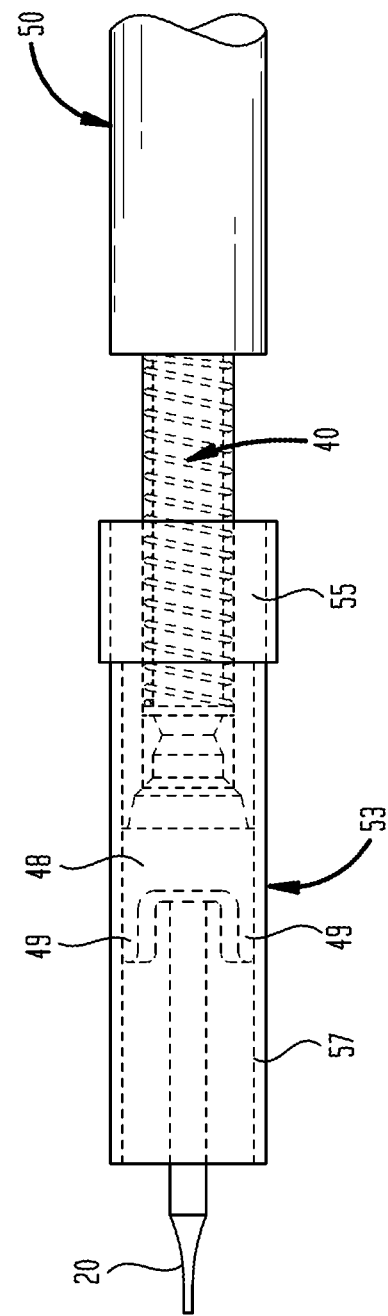
FIG. 4B is an elevational view depicting a portions of the cannula shown in FIGS. 2A-2B and the delivery tub of FIG. 3 together with a loading device during formation of the subassembly shown in FIG. 4A.

The subassembly shown in FIG. 4 can be made by threading the dilator through the seal of the delivery tube and advancing the dilator distally relative to the delivery tube beyond the position illustrated in FIG. 4. The cannula is then placed over the distal end of the dilator and advanced proximally until the cannula is positioned relative to the dilator as shown in FIG. 2, with the a part of the shaft of the dilator projecting out of the distal end of the cannula. When the cannula and delivery tube are in this position, the distal end mark 34 on the dilator is aligned with the distal end of the cannula. Once the cannula and dilator are in this position, the balloon 22 of the dilator is inflated so as to lock the cannula to the dilator. The cannula and dilator are then advanced proximally relative to the delivery tube. A guide 53 (FIG. 4B) may be used during this process. The guide is a tubular element open at both ends. A proximal section 55 of the guide has a bore with an inside diameter just slightly larger than the outside diameter of the delivery tube, whereas a distal section 57 has a bore with an inside diameter equal to or slightly less than the inside diameter of the delivery tube. The bores of sections 55 and 57 are concentric with one another. The operator may manually fold the arms 49 of anchor 48 to the collapsed condition as shown in FIG. 4B and position them within the bore of distal section 55. As the cannula and dilator are advanced proximally relative to the delivery tube, the delivery tube 50 enters the bore of proximal section 55. This aligns the bore of the distal section 57 concentric with the bore of the delivery tube. As the cannula and dilator are further advanced proximally, the arms 49 of the anchor pass into the delivery tube without catching on the distal edge of the delivery tube, and without damage to either structure. When the cannula and dilator are properly positioned within the delivery tube, the distal ends of the folded arms 49 of anchor 48 are aligned with or just proximal to the distal end of delivery tube 50.

To facilitate positioning of the cannula in the delivery tube, the fitting 54 at the proximal end of the delivery tube optionally may be provided with a stop which abuts the proximal end of the cannula when the cannula is properly positioned relative to the delivery tube. Alternatively, the seal 60 carried by the fitting may abut the proximal end of the delivery tube when the cannula is properly positioned.

Figure 8:
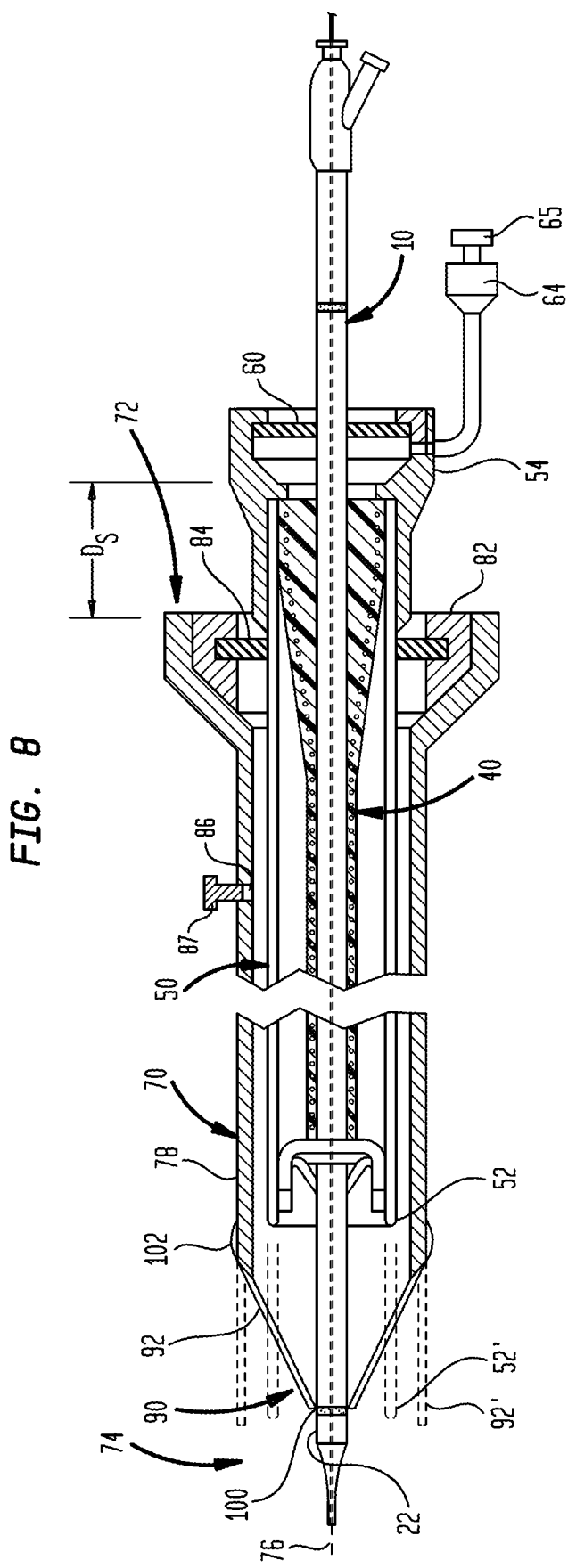
FIG. 8 is a fragmentary, diagrammatic sectional view of an assembly incorporating the components depicted in FIGS. 1-7 at one stage of operation.

The kit further includes a delivery sheath 70 (FIGS. 5-8). The delivery sheath has a proximal end 72 (FIGS. 7, 8), a distal end (FIGS. 5, 6, 8), and an axis 76 extending between the proximal and distal ends. The actuator has a tubular body with a wall 78 surrounding the axis and defining a bore 80 (FIGS. 6, 7) extending between the proximal and distal ends. Bore 80 has an interior diameter slightly larger than the exterior diameter of the delivery tube or actuator 50 (FIGS. 4, 8). For example, the interior diameter of the bore 80 may be about 12 mm, whereas the exterior diameter of sheath body 78 may be about 12.6 mm. The body desirably is formed from a relatively rigid polymer as, for example, a polymer of about 63 to about 72 Shore D hardness.

At the proximal end, the sheath 70 has a fitting 82 with a seal 84 (FIG. 7) adapted to engage the exterior surface of the delivery tube in a sliding, sealing fit. A purge port 86 extends through the wall 78 of the sheath adjacent its proximal end. A sealing plug 87 is releasably received in purge port 86.

At its distal end 74, the sheath includes an end element 90. The end element includes a plurality of flaps 92 distributed circumferentially around the axis 76 of the sheath. In the depicted embodiment, six flaps are used, of which three are visible in FIG. 5. More or fewer flaps may be used. In the closed position depicted in FIGS. 5 and 6, the flaps slope inwardly toward axis 76 from their proximal ends toward their distal ends, so that the flaps cooperatively define a surface that tapers in the distal direction, beyond the distal end of the body. The distal ends 96 of the flaps 92 cooperatively define a hole 100 at the distal extremity of the end element. This hole is coaxial with the axis 76 of the sheath body. In the embodiment depicted, the surface defined by the flaps is substantially in the form of a frustum of a cone, and the tear lines extend proximally and distally along the conical surface. The sloping surface defined by the flaps desirably lies at an angle A (FIG. 6) of about 10-30° to the axis 76. The end element itself may be formed integrally with the tubular body 78 or may be formed as a separate part that is joined to the body 78.

In the closed position, the flaps are connected to one another by frangible elements that releasably hold the flaps in the closed position. Preferably, the end element is formed as an integral unit from a polymeric material such as, and the frangible elements include simply weakened portions referred to herein as "tear lines" 98 (FIG. 5) between each paid of mutually adjacent flaps. For example, the tear lines may be formed by scoring inner or outer surface of the unitary element. Desirably, the scores used to form the tear lines extent only partially through the thickness of the end element. During use, the flaps will be forced apart and move to open positions in which the flaps extend generally parallel to axis 76, as shown in broken lines at 92' in FIG. 8. During this movement, each flap bends at its proximal end. The end element may include stress relief features such as circular holes or depressions (not shown) at the proximal ends of the tear lines 98 to help assure that the opening movement does not cause the flaps to break away from the wall of the tubular body. The surface formed by the flaps preferably is smooth and is fluid-impervious apart from hole 100. The flaps be covered by a film (not shown) which extends across the tear lines and covers any holes in the surface, so as to provide the smooth, impervious surface.

The sheath has a bump 102 or projection extending outwardly from the outer surface of body 80 at its distal end, adjacent the juncture with end element 90. This bump may be formed by the end element, by the body, or by an additional material deposited on the exterior of the body. The bump 102 desirably serves as a marker that can be visualized using an imaging modality. For example, where ultrasound is used to image the sheath during the implantation procedure, the bump desirably has an irregular surface pattern that can be discerned on an ultrasound image. Alternatively or additionally, the bump may be radiopaque so that it is visible in a fluoroscopic image. The sheath may also have one or more visible markings 104 on its exterior surface at predetermined points along its length.

The sheath, delivery tube, cannula and dilator are diagrammatically depicted in FIG. 8 in the assembled, operative condition, ready for implantation of the cannula within a patient. The subassembly including the delivery tube 50, cannula 40 and dilator 10 discussed above with reference to FIG. 4 is received within the sheath 70. The distal end of the dilator protrudes through the hole 100 at the distal extremity of the end element of the sheath, so that the tapered surface 20 of the dilator is disposed distal to the flaps 92 of the end element. The shaft of the dilator is received within hole 100, with a slight interference between the dilator and the distal ends of the flaps. Desirably, the dilator forms a fluid-tight seal with the end element. The proximal end of the dilator extends proximally beyond the proximally ends of the delivery tube and sheath. The proximal ends of the sheath and delivery tube are also closed fluid-tight, by seals 84 and 60. Thus, in the operative condition, cannula 40 is entirely contained within an enclosure defined by the sheath and delivery tube, and that enclosure is fluid-tight, apart from the purge ports on the sheath and delivery tube. In this operative condition, the dilator and cannula are locked together by the balloon on the dilator as discussed above with reference to FIG. 4. The fitting 54 on the proximal end of the delivery tube 50 is spaced proximally from the fitting 82 of the sheath.

In the operative condition shown in solid lines in FIG. 8, the delivery tube or actuator 50 is disposed in a disengaged position, with the distal end 52 of the delivery tube disposed proximal to the flaps 92 of the end element on the sheath. For example, the delivery tube may be in contact with the flaps. The distal end of the delivery tube is disposed adjacent the bump 102 of the outside of the sheath. In this operative condition, the fitting 54 on the delivery tube is spaced proximally from the fitting 82 on the sheath by a starting distance Ds. This starting distance should be greater than or equal to the amount of movement required to bring the delivery tube to the engaged position discussed below. The flaps can be moved from the closed position to an open position by retracting the sheath 70 relative to the patient while holding the delivery tube 50 in a fixed position relative to patient, so that the delivery tube moves distally relative to the sheath. This movement continues until the delivery tube is in an engaged position relative to the sheath, as partially depicted in broken lines in FIG. 8.

In this engaged position, the distal end of the delivery tube is in the position indicated at 52' in FIG. 8. As the sheath moves, the frangible elements such as score lines break and the flaps 92 are forced to pivot about their attachments to the body 78 of the sheath, so that the distal ends of the flaps move outwardly, away from axis 76 of the sheath. In the open position of the flaps, shown in broken lines at 92' in FIG. 8, the flaps extend generally parallel to the axis. During this movement, the cannula and dilator remain in fixed position with the delivery tube.

Optionally, the dimensions of the delivery tube and sheath may be selected so that the fitting 54 on the delivery tube abuts the fitting 82 on the sheath when the delivery tube reaches the engaged position. Thus, the fittings may serve as stops which prevent movement of the delivery tube beyond its engaged position. This arrangement can be used, for example, where the operator manually moves the sheath during use.

Figure 9:
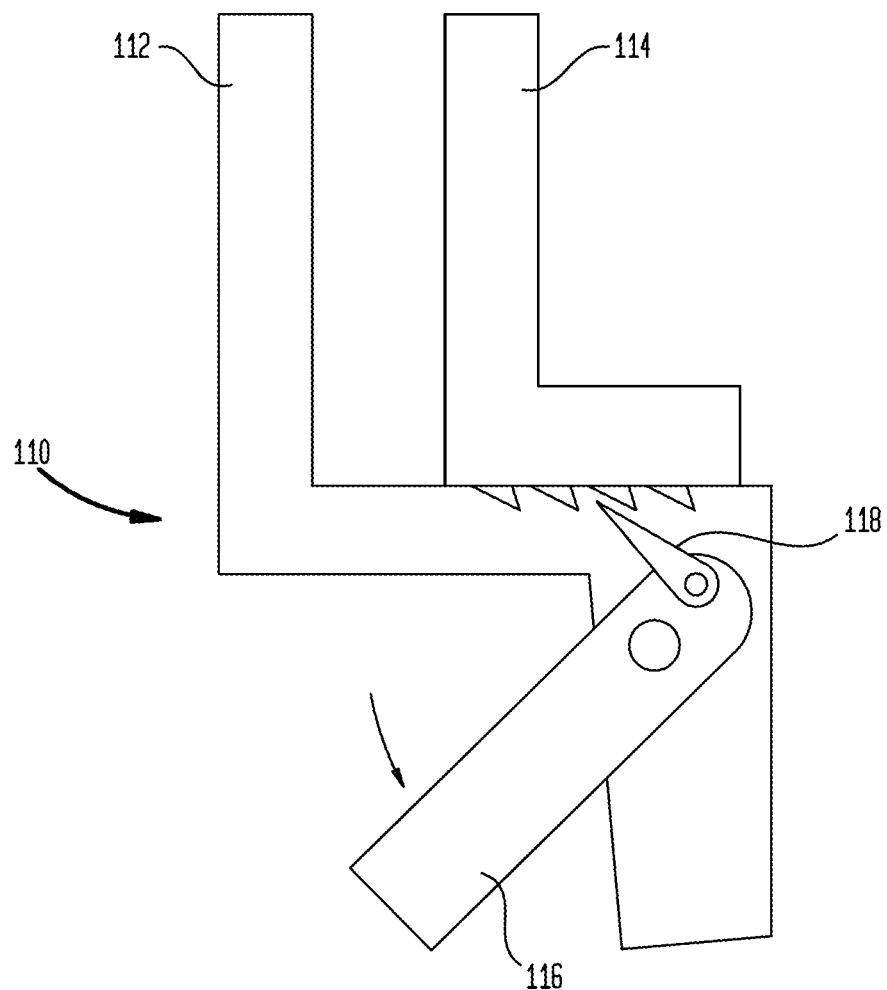
FIG. 9 is a diagrammatic elevational view of a drive mechanism usable in conjunction with the assembly of FIG. 8.

A drive mechanism 110, diagrammatically depicted in FIG. 9, may be provided for applying moving the sheath relative to the delivery tube. The drive mechanism includes a pair of jaws 112 and 114 adapted to engage the fittings of the delivery tube and sheath. The mechanism also includes an input element such as a handle 116 and a linkage 118 connected between the input element and the jaws, the linkage being arranged to force the jaws toward one another upon movement of the input element or handle 116. As depicted in FIG. 9, the mechanism includes a ratchet and pawl, and the handle is pivotably mounted to one of the jaws. However, any mechanical linkage which provides a mechanical advantage as, for example, a screw or gear mechanism, may be employed. The drive mechanism may include a pre-loaded spring which can be released to apply the required force. In a further alternative, the drive mechanism may include hydraulic, pneumatic or electrically-driven actuators. The jaws optionally may include features such as slots for receiving the fittings on the actuator and sheath. Alternatively, the fittings may include recesses and the jaws may include projections engagable within the recesses. The drive mechanism may be arranged to move the sheath through a predetermined distance relative to the delivery tube. In this case, the fittings on the delivery tube and sheath need not serve as stops, and desirably are spaced apart from one another by a starting distance Ds greater than the desired movement.

The kit desirably includes an external securement device 130, depicted in end view in FIG. 10 and in side view in FIG. 11. The securement device includes a split ring 132 including an exterior portion 131 formed from a stiff polymer and an interior portion 133 formed from a softer polymer. The split ring has a ring axis 134 and a slot 136 extending through the ring and extending parallel to the ring axis. The ring has an open condition shown in FIG. 10, in which the slot has a first width and a closed condition in which the slot has a second width less than the first width. The securement element includes a latch such as mating pin 138 and notch 140 on opposite side of the slot. When the split ring is in the closed condition, the pin 138 engages in the notch 140 and holds the split ring in the closed condition. The dimensions of the split ring are selected to that the split ring forms an interference fit with the section of the cannula 40 near its distal end when the ring is in the closed condition. However, the ring desirably can be forcibly moved along the cannula in the closed condition. The securement device 130 also includes a cuff 142 disposed at one end. The cuff is formed from a fabric or other material suitable for passage of sutures. The cuff material desirably is porous and promotes localized clotting and incorporation of cells within the material during the healing process. As explained below, the securement device is applied after placement of the cannula into the heart.

The kit may further include a forceps for use in maneuvering the cannula and the external securement element. The forceps 150 (FIG. 12) includes a pair of arms 152 pivotably relative to one another between the closed position shown in FIG. 12 and an open position. The arms pivot in a plane of motion parallel to the plane of the drawing in FIG. 12. Proximal ends of the arms are provided with gripping rings 154. The distal ends of the arms are curved out of the plane of motion, and are provided with jaws 156. Each jaw is defines a generally U-shaped channel so that when the jaws are in the closed position as depicted, they cooperatively define at least a portion of a tubular channel having an axis extending parallel or nearly parallel to the plane of motion of the arms. The channel desirably is sized to grasp the outside diameter of the distal portion of the cannula, but not to crush the cannula so as to damage it. The jaws are spaced from the plane of the arms 152 so that the axis 158 of the tubular channel defined by jaws 156 is spaced from the plane of arms 152. In an open position of the arms, the jaws are spaced apart from one another.

One sequence of operations which can be used to implant a cannula into a patient using the kit discussed above with reference to FIGS. 1-11 is as follows:

A small opening is formed in the patient's chest to expose the external surface of the heart at the desired chamber of the heart as, for example, the left atrium. A needle is inserted through the wall of the chamber, and a guidewire is inserted into the chamber. The guidewire may have a marking to indicate the desired depth of insertion. The needle is removed, leaving the guidewire in place with a proximal end of the guidewire extending out of the heart.

The assembly of the sheath, delivery tube, cannula and dilator, in the operative condition shown in FIG. 8, is flushed with saline solution by introducing the solution through the flushing port 64 (FIG. 3) of the delivery tube and allowing air to escape through the flushing port 86 of the sheath. These ports may then be closed by plugs 65 and 87. The sealed enclosure provided by the sheath and delivery tube allows the assembly to be flushed before it is brought into proximity to the patient. The assembly is "back-loaded" onto the guidewire, by threading the proximal end of the guidewire proximally through the guidewire lumen 18 (FIG. 1) of the dilator and through the guidewire port 28.

The entire assembly is manually advanced along the guidewire. As the distal end of the dilator penetrates the wall of the heart, the tapered surface 20 of the dilator (FIGS. 1, 8) forces the heart wall tissue outwardly, away from the axis. With continued advance of the assembly, the tapered surface defined by the flaps 92 of the end element on the sheath further forces the tissue outwardly, away from the axis 76 of the sheath. When the bump 102 (FIG. 6) on the distal end of the sheath passes through the wall of the heart, resistance to the advance decreases. This provides an indication to the operator that the assembly is correctly positioned. The positioning also may be confirmed by imaging, and by observing the position of the depth mark 104 (FIG. 5) on the sheath relative to the exterior of the heart.

At this point in the procedure, the flaps 92 of the end element on the sheath are disposed inside the heart chamber. Moreover, the distal end of the delivery tube is positioned inside the heart chamber. The flaps are then brought to the open position, preferably by retracting the sheath proximally relative to the heart, while maintaining the position of the delivery tube relative to the heart. The drive mechanism (FIG. 10) can be used to impel this motion.

After the flaps of the end element have been brought to their open position (92', FIG. 8) the cannula 40 can be advanced distally relative to the delivery tube 50 and sheath 70 by moving the dilator distally relative to those elements. Because the dilator is locked to the cannula by the balloon as discussed above, the cannula will move along with the dilator. When mark 36 on the dilator is aligned with the fitting 54 on the proximal end of the delivery tube, the distal end of the cannula 40 has advanced beyond the distal end of the delivery tube. This positioning can be confirmed by ultrasonic or other imaging. The arms of anchor 48 spring out to their expanded position (FIGS. 2A and 2B), so that the anchor will retain the distal end of the cannula within the heart.

While continuing to maintain the balloon on the dilator in its inflated state, so that the dilator remains locked to the cannula, the operator manually retracts the delivery tube 50 and sheath 70 proximally along the dilator, until they are proximal to distal section of the cannula the cannula. As the delivery tube and sheath are retracted, the heart wall closes around the cannula proximal to the anchor, forming a substantial tissue seal around the cannula. After retracting the delivery tube and sheath, the operator can grasp the cannula, either with his or her hands or with forceps 150 (FIG. 12), or both.

The operator can slip the external securement device 130 over the distal section of the cannula by passing holding the split ring 132 in the jaws of forceps 150, with the slot 136 (FIG. 12) of the split ring open, and moving the slot over the cannula transverse to its axis, until the cannula is inside the split ring. The operator can then close the split ring by moving the arms of the forceps toward the closed position. The split ring is placed on the cannula so that the cuff 142 faces toward the heart. Before or after closing the split ring, the operator can advance the split ring along the cannula until the cuff touches the wall of the heart. The operator may also suture the cuff to the heart wall. The offset between the jaws of forceps 150 and the plane of motion of the arms of the forceps keeps the arms of the forceps, and the operator's hand manipulating the forceps, out of the operator's line of sight and thus allows the operator to see the distal section of the cannula and the split ring during this process. Also, the partially-retracted sheath and delivery tube support and stabilize the cannula during this process. Once the external securement device 130 is in place, the wall of the organ is secured between the expanded anchor 48 engaging the interior of the heart wall and the external securement device on the exterior of the heart wall, so that cannula 40 is held in position. The operator then deflates the balloon on the dilator, thereby unlocking the dilator from the cannula, and retracts the dilator out of the cannula, carrying the sheath and delivery tube out of the way. The operator plugs the proximal end of the lumen in the cannula using a plug (not shown) to prevent blood loss.

The anchor on the cannula and the external locking device hold the distal end of the cannula in place. The proximal end of the cannula can be threaded though the patient's body to the location where the pump of the MCSD is to be placed, and connected to the pump. This is typically done by pulling the proximal end through a surgically-formed tunnel using a tool connected to the proximal end. For example, the plug inserted in the proximal end may have screw threads or other conventional features for engaging the pulling tool.

Numerous variations of the features discussed above can be used. For example, in the embodiment described above, the end element 90 in the closed position (FIG. 5) defines a conical surface with no openings apart from the central opening 100. This is highly desirable to facilitate purging of the system, but not essential in those applications where complete purging is not required. For example, there may be gaps between adjacent flaps when the flaps are in the closed position. Also, the flaps of the end element may be formed separately from one another. A frangible element used to hold the flaps in the closed position may be formed separately from the flaps. In a further variant, a release element such as a suture having an end accessible to the operator near the proximal end of the sheath may hold the flaps closed. The operator may operate the release element, as by pulling the suture out before bringing the flaps to the open position. In such an arrangement, the flaps optionally may be resiliently biased to the open position, so that they will move to the open position when the release element is removed. With this variant, the actuator or delivery tube is not required. In yet another variant, the flaps may be resiliently biased to the closed position, and may be forced to the open position by the actuator. The surface defined by the flaps need not be in the form of a cone or part of a cone; the surface may have a non-uniform taper. Also, in the embodiment above, the sheath, delivery tube, cannula and dilator all have generally circular cross-sectional shapes, but non-circular shapes may be employed.

In the embodiments above, the actuator used to move the flaps is the tube 50. However, the actuator need not be tubular. For example, individual rods may extend lengthwise within the sheath, each such rod being linked to one flap. The rods may be linked to one another, or may be individually movable by the operator. In any such arrangement, the surfaces surrounding the anchors on the cannula desirably are smooth so that the anchors will not be damaged and will deploy smoothly. In yet another variant, the actuator may be omitted and other means may be used to move the flaps to the open position. For example, an additional balloon can be placed around the distal end of the dilator, so that the additional balloon is disposed distal to the cannula, inside the end element. Such a balloon can be inflated momentarily to open the flaps and then deflated.

The dilator 10 used in the embodiments discussed above is not essential. For example, flaps 92 of the end element of the sheath may form a surface which tapers to a point, with no central opening or with only a very small opening for a guidewire.

The device placed using the kit need not be a cannula as discussed above. Any other device can be placed. For example, certain MCSDs use pumps which can be placed partially or fully within a chamber of the heart. A pump of this type can be positioned within the sheath and placed using the device. Also, the device may be placed into hollow organs other than the heart.

In the embodiments discussed above, a balloon on the dilator serves to releasably lock the dilator and cannula together. However, other structures which can perform this function may be employed. For example, the dilator may be provided with a mechanical element such as a basket which can be expanded and contracted using a control element accessible at the proximal end of the dilator.

In the embodiments discussed above, the external securement device 130 is placed on the cannula after the cannula has been implanted, as by passing the slot 136 of the split ring (FIG. 10) over the cannula. In a further variant, the external securement device may be disposed on the cannula, remote from the distal end of the cannula, before the cannula is implanted. In such an arrangement, the external securement device may be a simple closed ring 230 (FIG. 13). In the open condition shown in solid lines, ring 230 has an inside diameter slightly larger than the outside diameter of the cannula 240, so that the ring forms a free-running fit with the cannula at least near the distal end. Where the cannula has a tapered outside diameter, the ring in the open condition may frictionally engage the cannula at its larger, proximal end, so that the ring will remain in place during implantation. The ring can be deformed to the closed position shown in broken lines by crimping the ring, using a forceps or similar instrument. In the closed position, the ring will engage the distal end of the cannula with a tight fit. For example, the ring may be formed from a material which can be plastically deformed in the transition from the open condition to the closed condition. In further variants, the cannula may have a series of ridges (not shown) projecting outwardly on its exterior surface adjacent its distal end, and the external securement device may have corresponding ridges on its interior surface. In this embodiment, the ridges on the cannula mechanically engage with the ridges on the external securement device when the external securement device is brought to the closed position. External securement devices as described herein can be used with a cannula regardless of how the distal end of the cannula is implanted in the organ of the subject.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention. Certain aspects of the present invention are further described in the appended claims.

INDUSTRIAL APPLICABILITY

The present invention can be applied in medical and veterinary treatment.

The invention claimed is:

1. An assembly, comprising:
   an enclosure including a sheath having a proximal end and a distal end, wherein the sheath defines an axis extending between the proximal end of the sheath and the distal end of the sheath, and wherein the sheath includes a wall defining a bore extending along the axis to the distal end of the sheath; and
   an end element disposed at the distal end of the sheath, the end element including a plurality of flaps having proximal ends attached to the wall of the sheath at the distal end of the sheath and distal ends remote from the sheath, the flaps being in a closed position in which the flaps slope inwardly toward the axis from their proximal ends toward their distal ends so that the flaps cooperatively define a surface tapering in the distal direction beyond the distal end of the sheath, the flaps being displaceable so as to move the distal ends of the flaps away from the axis and pivot the flaps to an open position;
   an elongated cannula having proximal and distal ends and a lumen, the cannula being configured to be contained within the enclosure with the distal end of the cannula disposed proximate the distal end of the sheath;
   a dilator having a distal portion configured to be disposed within the lumen of the cannula with a proximal portion of the dilator extending proximally beyond the proximal end of the cannula, the dilator being configured to form a fluid-tight seal with the end element when the dilator is disposed within the cannula and the cannula is contained within the enclosure, and the dilator slideable proximally and distally relative to the sheath; and
   a locking element configured to secure the cannula and the dilator together.

2. The assembly of claim 1, wherein the locking element is configured to releasably secure the cannula and the dilator together.

3. The assembly of claim 1, further comprising an actuator configured to be disposed within the bore of the sheath in a disengaged position, the actuator being movable relative to the sheath from the disengaged position to an engaged position, wherein the actuator is configured to force the flaps from the closed position to the open position as the actuator moves to the engaged position.

4. The assembly of claim 3, wherein the actuator includes a delivery tube, and wherein the cannula is configured to be disposed within the delivery tube.

5. The assembly of claim 1, wherein the sheath defines one or more purge ports configured to communicate with an interior portion of the enclosure.

6. The assembly of claim 1, wherein the dilator includes a tapered tip at its distal end, and wherein the plurality of flaps are configured to define a hole at a distal end of the surface when the flaps are in the closed position, and wherein the dilator is configured to extend through the hole.

7. An assembly comprising:
   a sheath having a body with proximal and distal ends, an axis extending between the proximal and distal ends and a wall defining a bore extending along the axis to the distal end of the body;
   an end element disposed at a distal end of the bore, the end element including a plurality of flaps having proximal ends attached to the wall of the body at the distal end of the body and distal ends remote from the body, the flaps being in a closed position in which the flaps slope inwardly toward the axis from their proximal ends toward their distal ends so that the flaps cooperatively define a surface tapering in the distal direction beyond the distal end of the body, the flaps being displaceable so as to move the distal ends of the flaps away from the axis and pivot the flaps to an open position;
   a delivery tube configured to position within the bore, wherein the sheath and the delivery tube define an enclosure when the delivery tube is within the bore;
   a fitting on a proximal end of the delivery tube;
   a cannula having proximal and distal ends and a lumen, the cannula being configured to be entirely contained within the enclosure with the distal end of the cannula disposed adjacent the distal end of the sheath; and
   a shaft having a distal portion configured to be disposed within the lumen of the cannula with a proximal portion of the shaft extending proximally beyond the proximal end of the cannula, the shaft being configured to sealingly engage with the fitting, and the shaft slideable proximally and distally relative to the sheath.

8. The assembly of claim 7, further comprising a locking mechanism adapted to releasably lock the shaft and the cannula together.

9. The assembly of claim 7, wherein the delivery tube is movable relative to the sheath from a disengaged position to an engaged position, and wherein the delivery tube is configured to force the flaps from the closed position to the open position as the delivery tube moves to the engaged position.

10. The assembly of claim 7, wherein the delivery tube includes a distal end configured to be disposed within the sheath proximal to the flaps and a proximal portion projecting proximally from the sheath, wherein the proximal portion is in slideable sealing engagement with the sheath.

11. The assembly of claim 7, wherein at least one of the body of the sheath, the delivery tube, or the fitting defines one or more purge ports configured to communicate with an interior portion of the enclosure.

12. The assembly of claim 7, wherein the shaft is a portion of a dilator, the dilator including a tapered tip.

13. The assembly of claim 12, wherein the plurality of flaps of the sheath define a hole at a distal end of the surface when the flaps are in the closed position, and where the dilator is extendable through the hole.

14. A delivery sheath for a medical device comprising:
a tubular body having proximal and distal ends, an axis extending between the proximal and distal ends, a wall defining an exterior surface, and a bore extending along the axis to the distal end of the tubular body;
an end element disposed at a distal end of the bore, the end element including a plurality of flaps having proximal ends attached to the wall of the tubular body at the distal end of the tubular body and distal ends remote from the tubular body, the flaps having a closed position in which the flaps slope inwardly toward the axis from their proximal ends toward their distal ends so that the flaps cooperatively define a surface tapering in the distal direction beyond the distal end of the tubular body, the flaps being displaceable so as to move the distal ends of the flaps away from the axis and pivot the flaps to an open position, wherein the plurality of flaps are configured to define a hole at a distal end of the surface tapering in the distal direction when the plurality of flaps are in the closed position; and
a bump projecting outwardly from the exterior surface at the distal end of the tubular body, wherein the bump has an irregular surface pattern, the irregular surface pattern being configured to be discerned on an ultrasound image.

15. The delivery sheath of claim 14, wherein the bore has a diameter of approximately 12 millimeters.

16. The delivery sheath of claim 14, wherein the hole is coaxial with the axis.

17. The delivery sheath of claim 14, wherein the bump is made from a radiopaque material.

18. The delivery sheath of claim 14, wherein the plurality of flaps comprises six flaps.

19. The delivery sheath of claim 14, wherein the plurality of flaps are covered in a film configured to provide an impervious surface.

* * * * *